United States Patent
Attal et al.

(10) Patent No.: US 9,927,375 B2
(45) Date of Patent: Mar. 27, 2018

(54) SYSTEM AND METHOD FOR PRINTABILITY BASED INSPECTION

(71) Applicant: Applied Materials Israel, Ltd., Rehovot (IL)

(72) Inventors: Shay Attal, Rehovot (IL); Ori Petel, Ramat-Gan (IL); Sergey Latinsky, Modiin (IL); Sergey Khristo, Ashdod (IL); Boaz Cohen, Lehavim (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 142 days.

(21) Appl. No.: 14/977,379

(22) Filed: Dec. 21, 2015

(65) Prior Publication Data

US 2017/0176347 A1  Jun. 22, 2017

(51) Int. Cl.
*G01N 21/00* (2006.01)
*G01N 21/956* (2006.01)
*G01N 21/88* (2006.01)

(52) U.S. Cl.
CPC ....... *G01N 21/956* (2013.01); *G01N 21/8851* (2013.01); *G01N 2021/95676* (2013.01)

(58) Field of Classification Search
CPC ............. G01N 21/956; G01N 21/8851; G01N 2021/95676
USPC ...................................................... 356/237.5
See application file for complete search history.

(56) References Cited

U.S. PATENT DOCUMENTS

| | | | |
|---|---|---|---|
| 7,369,236 B1 * | 5/2008 | Sali | G01N 21/95607 356/237.1 |
| 2007/0196747 A1 * | 8/2007 | Granik | G03F 1/36 430/30 |
| 2008/0052021 A1 * | 2/2008 | Morinaga | G01N 21/8851 702/81 |
| 2014/0063478 A1 * | 3/2014 | Manka | G03F 7/70641 355/55 |
| 2016/0019689 A1 * | 1/2016 | Inoue | G06T 7/001 382/149 |

* cited by examiner

*Primary Examiner* — Hina F Ayub
(74) *Attorney, Agent, or Firm* — Kilpatrick Townsend & Stockton LLP

(57) ABSTRACT

According to an embodiment of the invention there may be provided a system for assigning lithographic mask inspection process parameters. The system may include a search module, a decision module and a memory module. The memory module may be configured to store an expected image expected to be formed on a photoresist during a lithographic process that involves illuminating the lithographic mask. The search module may be configured to search in the expected image for printable features. The decision module may be configured to assign a first lithographic mask inspection process parameter to lithographic mask areas related to printable features and assign a second lithographic mask inspection process parameter to at least some lithographic mask areas that are not associated with printable features. The second lithographic mask inspection process parameter may differ from the first lithographic mask inspection process parameter.

13 Claims, 8 Drawing Sheets

101

```
┌─────────────────────────────────────────────────────────────────┐
│  Generating or receiving an expected image formed on a          │
│  photoresist during a lithographic process that involves        │
│  illuminating the lithographic mask 210                         │
└─────────────────────────────────────────────────────────────────┘
                                │
                                ▼
┌─────────────────────────────────────────────────────────────────┐
│  Searching in the expected image for printable features. When   │
│  using a positive tone photoresist each printable feature has a │
│  local minimum that is below a first intensity threshold and    │
│  comprises pixels that have an intensity that does not exceed   │
│  the second threshold.                                          │
│  When using a negative tone photoresist each printable feature  │
│  has a local maximum that is above the first intensity          │
│  threshold and comprises pixels that have an intensity value    │
│  that is not lower than the second intensity threshold. The     │
│  first intensity threshold exceeds the second intensity         │
│  thresholds                                                     │
│                              220                                │
└─────────────────────────────────────────────────────────────────┘
                                │
                                ▼
┌─────────────────────────────────────────────────────────────────┐
│  Assigning a first lithographic mask inspection process         │
│  parameter to be applied during an inspection of lithographic   │
│  mask areas that related to printable features; and assigning   │
│  a second lithographic mask inspection process parameter to at  │
│  least some lithographic mask areas that are not related to     │
│  printable features 230                                         │
└─────────────────────────────────────────────────────────────────┘
                                │
                                ▼
┌─────────────────────────────────────────────────────────────────┐
│  Inspecting the lithographic mask while applying the first      │
│  lithographic mask inspection process parameter when            │
│  inspecting lithographic mask areas related to printable        │
│  features and while applying a second lithographic mask         │
│  inspection process parameter to lithographic mask areas that   │
│  are not associated with printable features.                    │
│                              240                                │
└─────────────────────────────────────────────────────────────────┘
```

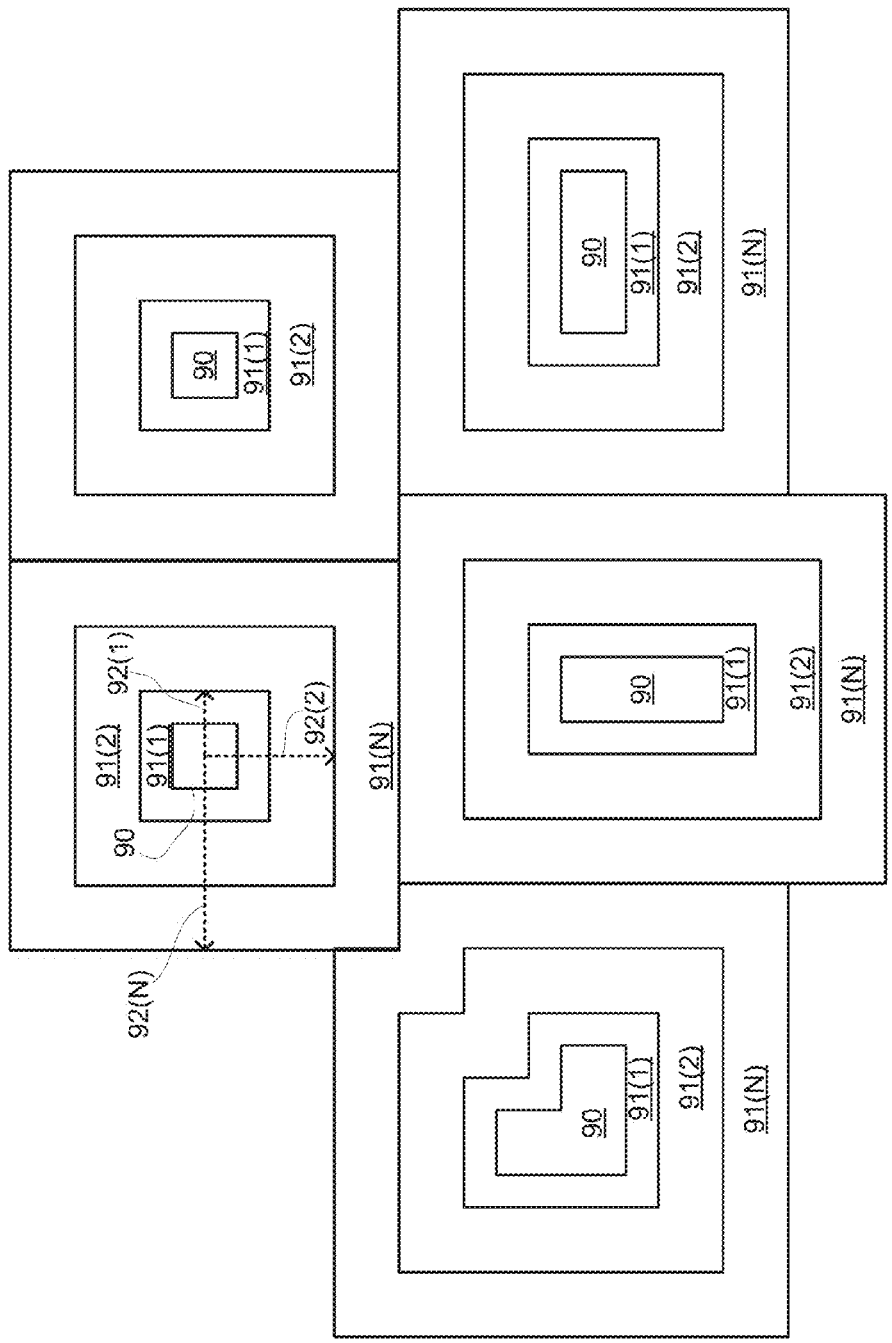

SYSTEM AND METHOD FOR PRINTABILITY BASED INSPECTION

BACKGROUND

Lithographic masks are exposed during a lithographic process to radiation thereby forming patterns on a wafer.

A lithographic mask error may result in a large number of defective wafers.

On one hand there is a need to rigorously inspect lithographic masks as the cost associated with lithographic masks error is high.

On the other hand the inspection of the lithographic process should be relatively fast.

There is a growing need to provide accurate and fast methods for inspecting a lithographic mask.

SUMMARY

According to an embodiment of the invention there may be provided a system for assigning lithographic mask inspection process parameters, the system may include a search module, a decision module and a memory module; wherein the memory module may be configured to store an expected image expected to be formed on a photoresist during a lithographic process that involves illuminating the lithographic mask; wherein the search module may be configured to search in the expected image for printable features, and wherein the decision module may be configured to assign a first lithographic mask inspection process parameter to lithographic mask areas related to printable features and assign a second lithographic mask inspection process parameter to at least some lithographic mask areas that are not associated with printable features; and wherein the second lithographic mask inspection process parameter differs from the first lithographic mask inspection process parameter.

Each printable feature may have a local minimum that is below a first intensity threshold and may include pixels that have intensity that do not exceed a second intensity threshold; wherein the first intensity threshold is lower than the second intensity threshold.

The second intensity threshold may be a printability threshold of the lithographic mask.

The system may include an inspection module that may be configured to inspect the lithographic mask while applying the first lithographic mask inspection process parameter when inspecting lithographic mask areas related to printable features and while applying a second lithographic mask inspection process parameter to lithographic mask areas that are not associated with printable features.

The first lithographic mask inspection process parameter and the second lithographic mask inspection process parameters may define a sensitivity of the inspection process.

Each printable feature may have a local maximum that is above a first intensity threshold and may include pixels that have an intensity that are not lower than a second intensity threshold; wherein the first intensity threshold is higher than the second intensity threshold.

According to an embodiment of the invention there may be provided a method for assigning lithographic mask inspection process parameters, the method may include generating or receiving an expected image that is expected to be formed on a photoresist during a lithographic process that involves illuminating the lithographic mask; searching in the expected image for printable features; assigning a first lithographic mask inspection process parameter to be applied during an inspection of lithographic mask areas that related to printable features; and assigning a second lithographic mask inspection process parameter to at least some lithographic mask areas that are not related to printable features.

Each printable feature may have a local minimum that is below a first intensity threshold and may include pixels that have intensity that do not exceed a second intensity threshold.

The second intensity threshold may be a printability threshold of the lithographic mask.

The method may include receiving an intensity value; and calculating the first intensity threshold and the second intensity threshold in response to the intensity value, a distance between the first intensity threshold and the second intensity threshold, and a distribution of pixels of the expected images between the first intensity threshold and the second intensity threshold.

The calculating may include searching for a tradeoff between a (a) the distance between the first intensity threshold and the second intensity threshold and (b) an amount of pixels of the expected images between the first intensity threshold and the second intensity threshold.

The method may include assigning the second lithographic mask inspection process parameter to lithographic mask areas that are within a first distance from printable feature; and assigning a third lithographic mask inspection process parameter to lithographic mask areas that are positioned at second distance from a printable feature, the second distance exceeds the first distance.

The method may include inspecting the lithographic mask while applying the first lithographic mask inspection process parameter when inspecting lithographic mask areas related to printable features and while applying the second lithographic mask inspection process parameter to lithographic mask areas that are not associated with printable features.

A first lithographic mask inspection process parameter and the second lithographic mask inspection process parameter may define a sensitivity of the inspection process.

A first lithographic mask inspection process parameter and the second lithographic mask inspection process parameter may define a relationship between a false alarm ratio of the inspection process and a sensitivity of the inspection process.

Each printable feature may have a local maximum that is above a first intensity threshold and may include pixels that have an intensity that are not lower than a second intensity threshold; wherein the first intensity threshold is higher than the second intensity threshold.

According to an embodiment of the invention there may be provided a non-transitory computer readable medium that may store instructions that once executed by a computer cause the computer to generate or receive an expected image that is expected to be formed on a photoresist during a lithographic process that involves illuminating a lithographic mask; search in the expected image for printable features; assign a first lithographic mask inspection process parameter to be applied during an inspection of lithographic mask areas that related to printable features; and assign a second lithographic mask inspection process parameter to at least some lithographic mask areas that are not related to printable features.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3 illustrates a method according to an embodiment of the invention;

FIG. 6 illustrates various areas of a lithographic mask according to an embodiment of the invention.

Figure 1A:
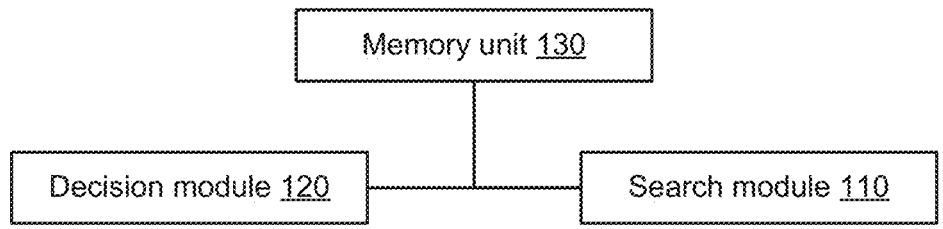
FIG. 1A illustrates a system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The phrase "area associated with a printable feature" refers to an area of a lithographic mask that once illuminated, during a lithographic process, results in a formation of printable feature on a photoresist. The phrase "area associated with a non-printable feature" refers to an area of a lithographic mask that once illuminated, during a lithographic process, does not result results in a formation of printable feature on a photoresist.

FIG. 1A illustrates system 101 according to an embodiment of the invention.

System 101 may be a desktop computer, a server, a laptop computer, a mobile computerized system, a combination of computers, and the like.

System 101 includes search module 110, decision module 120 and memory module 130.

Search module 110 and decision module 120 may be one or more hardware processors or may be hosted by one or more hardware processors that are configured to execute instructions that facilitate searching for printable features and for assigning different lithographic mask inspection process parameter to different areas of the lithographic mask.

A lithographic mask inspection process parameter is a parameter that is applied during an inspection process of a lithographic mask. The parameter may be a sensitivity of the inspection process, a false alarm ratio of the inspection process, a signal to noise ration of the inspection process, a resolution of the inspection process, and the like.

According to an embodiment of the invention areas of the lithographic masks that are associated with printable features should be examined with higher accuracy than areas of the lithographic mask that are associated with non-printable features.

The lithographic mask can be partitioned to multiple types of lithographic mask areas, the partitioning may be based upon the distance of the printable features.

Memory module 130 is configured to store an expected image that is expected to be formed on a photoresist during a lithographic process that involves illuminating the lithographic mask. The expected image may be an Aerial image of the lithographic mask.

Search module 110 is configured to search, in the expected image, for printable features. Each printable feature has a local minimum that is below a first intensity threshold and comprises pixels that have an intensity that does not exceed a second intensity threshold. The first intensity threshold is lower than the second intensity threshold.

Decision module 120 is configured to assign a first lithographic mask inspection process parameter to lithographic mask areas related to printable features and assign a second lithographic mask inspection process parameter to at least some lithographic mask areas that are not associated with printable features. The second lithographic mask inspection process parameter differs from the first lithographic mask inspection process parameter.

The second intensity threshold may be a printability threshold of the lithographic mask.

It is noted that more than three different lithographic mask inspection process parameters may be assigned to more than three different areas of the lithographic mask. The assignment can be responsive, for example, to distances between the different areas of the lithographic masks to printable features of the lithographic mask.

It is noted that different lithographic mask inspection process parameters may be assigned to different areas within the printability areas. The allocation of different lithographic mask inspection process parameters within a printability area may be responsive to a distance from a border of the printability area, to a distance from a center of the printability area, to a shape and/or size of the printability area, and the like.

Figure 1B:
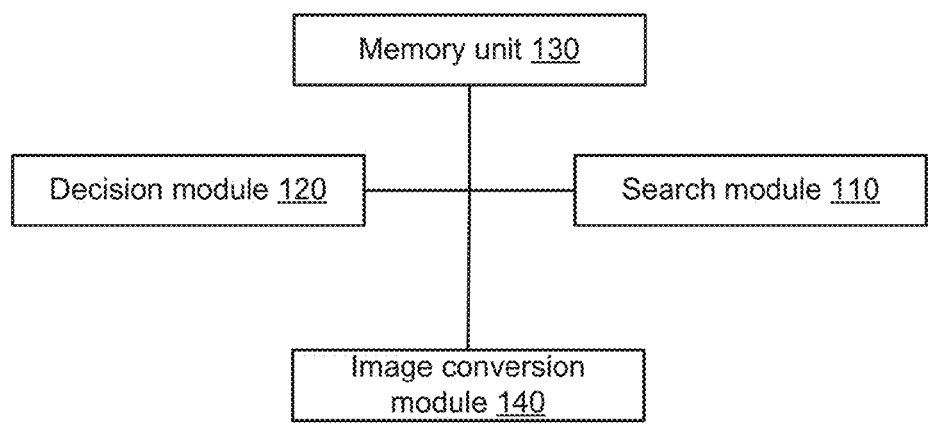
FIG. 1B illustrates a system according to an embodiment of the invention.

FIG. 1B illustrates system 102 according to an embodiment of the invention.

System 101 includes search module 110, decision module 120, memory module 130, and also includes image conversion module 140.

Image conversion module 140 is configured to receive an image of the lithographic mask (that is not the expected image that is expected to be formed on the photoresist during the lithographic process that involves illuminating the lithographic mask) and convert the image of the lithographic mask to the expected image that is expected to be formed on the photoresist during the lithographic process that involves illuminating the lithographic mask. In general, this model can simulate aerial, smooth aerial images and inverted negative tone masks.

The image conversion module 140 may be an Aerial simulator. The image conversion module 140 may be one or more hardware processors or may be hosted by one or more hardware processors.

There may be two types of resists—positive tone resists and negative tone resists. When using a negative tone resists the lithographic mask contains the pattern which is to remain on the wafer. When using a positive tone resists the lithographic mask contains an inverse or negative of the pattern which is to remain on the wafer.

In the specification it is assumed that positive tone resist is used. It is noted that any of the methods, systems and computer readable medium can be applied, mutatis mutandis, when using negative tone resists.

When using a positive tone resists each printable feature has a local minimum that is below the first intensity threshold and includes pixels that have an intensity that do not exceed the second intensity threshold. The second intensity threshold exceeds the first intensity threshold.

When using negative tone photoresist each printable feature has a local maximum that is above the first intensity threshold and comprises pixels that have an intensity value that are not lower than the second intensity threshold. The first intensity threshold exceeds the second intensity thresholds.

The image conversion module 140 may invert an expected image of a negative tone photoresist before processing the expected image.

Figure 1C:
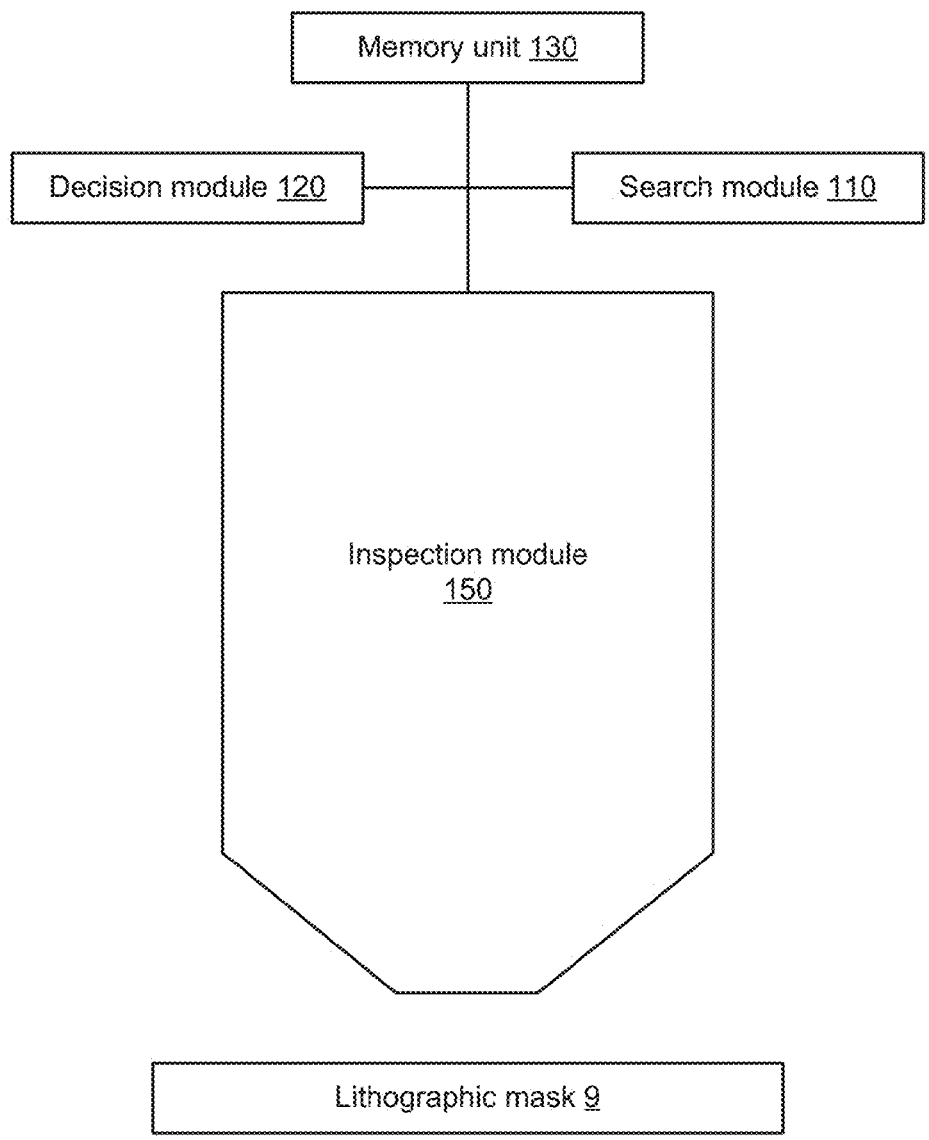
FIG. 1C illustrates a system and a lithographic mask according to an embodiment of the invention.

FIG. 1C illustrates system 103 and lithographic mask 9 according to an embodiment of the invention.

System 103 includes search module 110, decision module 120, memory module 130, and also includes inspection module 150.

Inspection module 150 is configured to inspect the lithographic mask while applying the first lithographic mask inspection process parameter when inspecting lithographic mask areas related to printable features and while applying a second lithographic mask inspection process parameter to lithographic mask areas that are not associated with printable features. The mask may be virtually partitioned to more than two types of area.

The inspection module 150 may generate the expected image, and additionally or alternatively, may generate an image of the photolithographic mask that is received by the image conversion module 140 (and is converted by the image conversion module). Alternatively—the expected image and/or the image of the photolithographic mask that is received by the image conversion module 140 may be generated by a module that differs from the inspection module 150.

Inspection module 150 may acquire the expected image using one or more beams of electromagnetic radiation. The electromagnetic radiation may be, for example, visible light radiation, ultra violet radiation, deep ultraviolet radiation, extreme ultraviolet radiation, electron beam radiation, infrared radiation, and the like.

Figure 2:
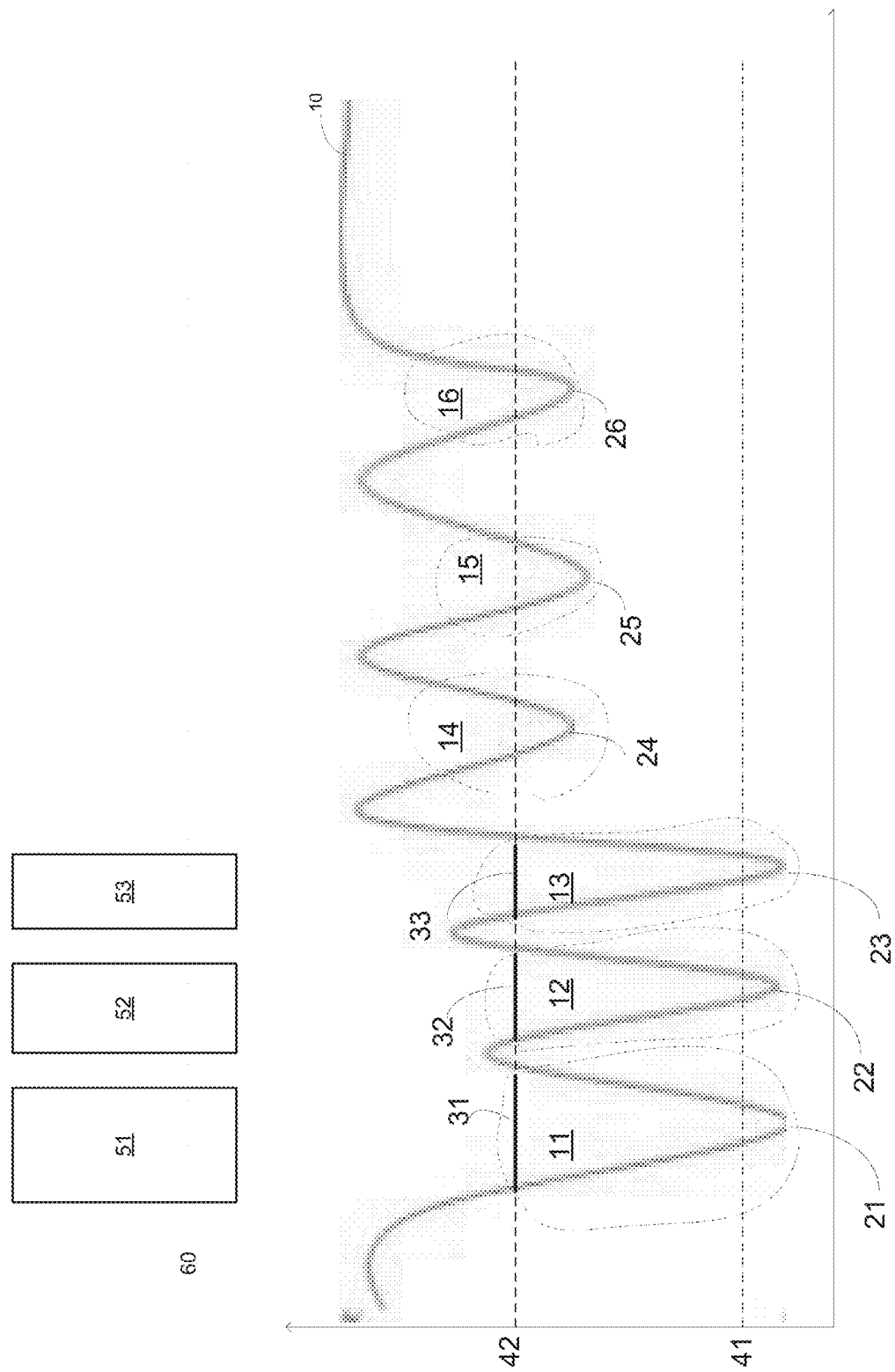
FIG. 2 illustrates an intensity of pixels of an expected image along a line that crosses three printable features, according to an embodiment of the invention.

FIG. 2 illustrates an intensity of pixels of an expected image along line 60 that crosses printable features 51, 52 and 53, according to an embodiment of the invention.

The printable features 51, 52 and 53 may be pads or may be portions of lines.

Curve 10 has six segments 11, 12, 13, 14, 15 and 16 having local minima 21, 22, 23, 24, 25 and 26.

FIG. 2 also illustrates first intensity threshold 41 and second intensity threshold 42. First intensity threshold 41 is lower than second intensity threshold 42.

The expected image may include printable features and non-printable features.

A printable feature has a local minimum that is below first intensity threshold 41 and include pixels that have an intensity that do not exceed the second intensity threshold 42.

Segments 11, 12 and 13 have local minima 21, 22 and 23 below first intensity threshold 41 and include pixels that have an intensity that does not exceed the second intensity threshold 42 and thus are a part of printable features.

Lines 31, 32 and 33 illustrate portions of conductors that are printed—these lines represent pixels that have an intensity that does not exceed the second intensity threshold 42. Lines 31, 32 and 33 are intersection between segments 11, 12 and 13 and second intensity threshold 42 and represent the intersection of line 60 with printable features 51, 52 and 53.

Segments 14, 15 and 16 have an upper portion that crosses second intensity threshold 42 but their local minima 24, 25 and 26 are above first intensity threshold 41 and are a not a part of printable features.

FIG. 3 illustrates method 200 according to an embodiment of the invention.

Method 200 may start by step 210 of generating or receiving an expected image that is expected to be formed on a photoresist during a lithographic process that involves illuminating the lithographic mask.

The expected image may be an aerial image of the lithographic mask.

Step 210 may be followed by step 220 of searching in the expected image for printable features.

When using positive tone photoresist each printable feature has a local minimum that is below the first intensity threshold and includes pixels that have an intensity that do not exceed the second intensity threshold. The second intensity threshold exceeds the first intensity threshold.

When using negative tone photoresist each printable feature has a local maximum that is above the first intensity threshold and comprises pixels that have an intensity value that are not lower than the second intensity threshold. The first intensity threshold exceeds the second intensity thresholds.

The second intensity threshold may be a printability threshold of the lithographic mask.

Step 220 may be followed by step 230 of assigning a first lithographic mask inspection process parameter to be applied during an inspection of lithographic mask areas that related to printable features; and assigning a second lithographic mask inspection process parameter to at least some lithographic mask areas that are not related to printable features.

Step 230 may include assigning the second lithographic mask inspection process parameter to lithographic mask areas that are within a first distance from printable feature; and assigning a third lithographic mask inspection process parameter to lithographic mask areas that are positioned at second distance from a printable feature, the second distance exceeds the first distance.

It is noted that more than three different lithographic mask inspection process parameters may be assigned to more than three different areas of the lithographic mask. The assignment can be responsive, for example, to distances between the different areas of the lithographic masks to printable features of the lithographic mask.

It is noted that different lithographic mask inspection process parameters may be assigned to different areas within the printability areas. The allocation of different lithographic mask inspection process parameters within a printability area may be responsive to a distance from a border of the printability area, to a distance from a center of the printability area, to a shape and/or size of the printability area, and the like.

Step 230 may be followed by step 240 of inspecting the lithographic mask while applying the first lithographic mask inspection process parameter when inspecting lithographic mask areas related to printable features and while applying a second lithographic mask inspection process parameter to lithographic mask areas that are not associated with printable features.

According to an embodiment of the invention a user may set the first and second intensity thresholds. According to another embodiment of the invention the user may provide an initial intensity value and the first and second intensity thresholds are calculated. A non-limiting example of a calculation of the first and second intensity thresholds is provided in FIG. 4.

Figure 4:
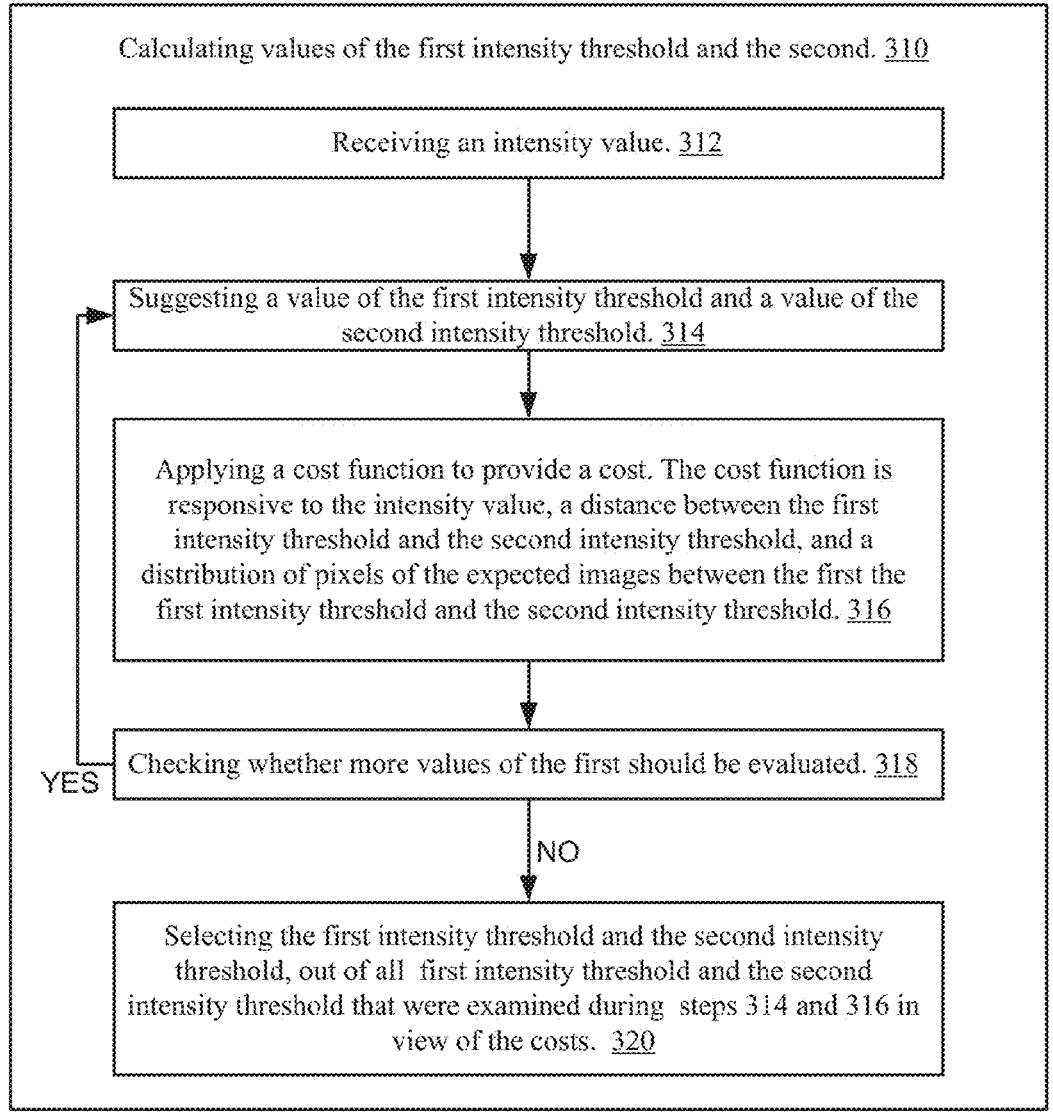
FIG. 4 illustrates a method according to an embodiment of the invention.

FIG. 4 illustrates method 300 according to an embodiment of the invention.

Method 300 includes step 310 of calculating values of the first intensity threshold and the second intensity threshold in response to an initial intensity value provided by a user.

Step 310 may include steps 312, 314, 316, 318 and 320.

Step 312 may include receiving an intensity value.

Step 312 may be followed by step 314 of suggesting a value of the first intensity threshold and a value of the second intensity threshold. During a first iteration of step 314 the suggested values may be default values. During next iterations of step 314 that suggested values may be responsive to previously evaluated values.

Step 314 may be followed by step 316 of applying a cost function to provide a cost. The cost function is responsive to the intensity value, a distance between the first intensity threshold and the second intensity threshold, and a distribution of pixels of the expected images between the first intensity threshold and the second intensity threshold.

The cost function may be aimed to find a tradeoff between a (a) the distance between the first intensity threshold and the second intensity threshold and (b) an amount of pixels of the expected image between the first intensity threshold and the second intensity threshold.

For example the cost function may equal a weighted sum of the distance between the first intensity threshold and the second intensity threshold, and the amount of pixels of the expected image between the first intensity threshold and the second intensity threshold.

The cost function may be configured to increase the distance between the first intensity threshold and the second intensity threshold up to a maximal allowable distance while reducing the number of pixels of the expected image that are between the first intensity threshold and the second intensity threshold.

Figure 5:
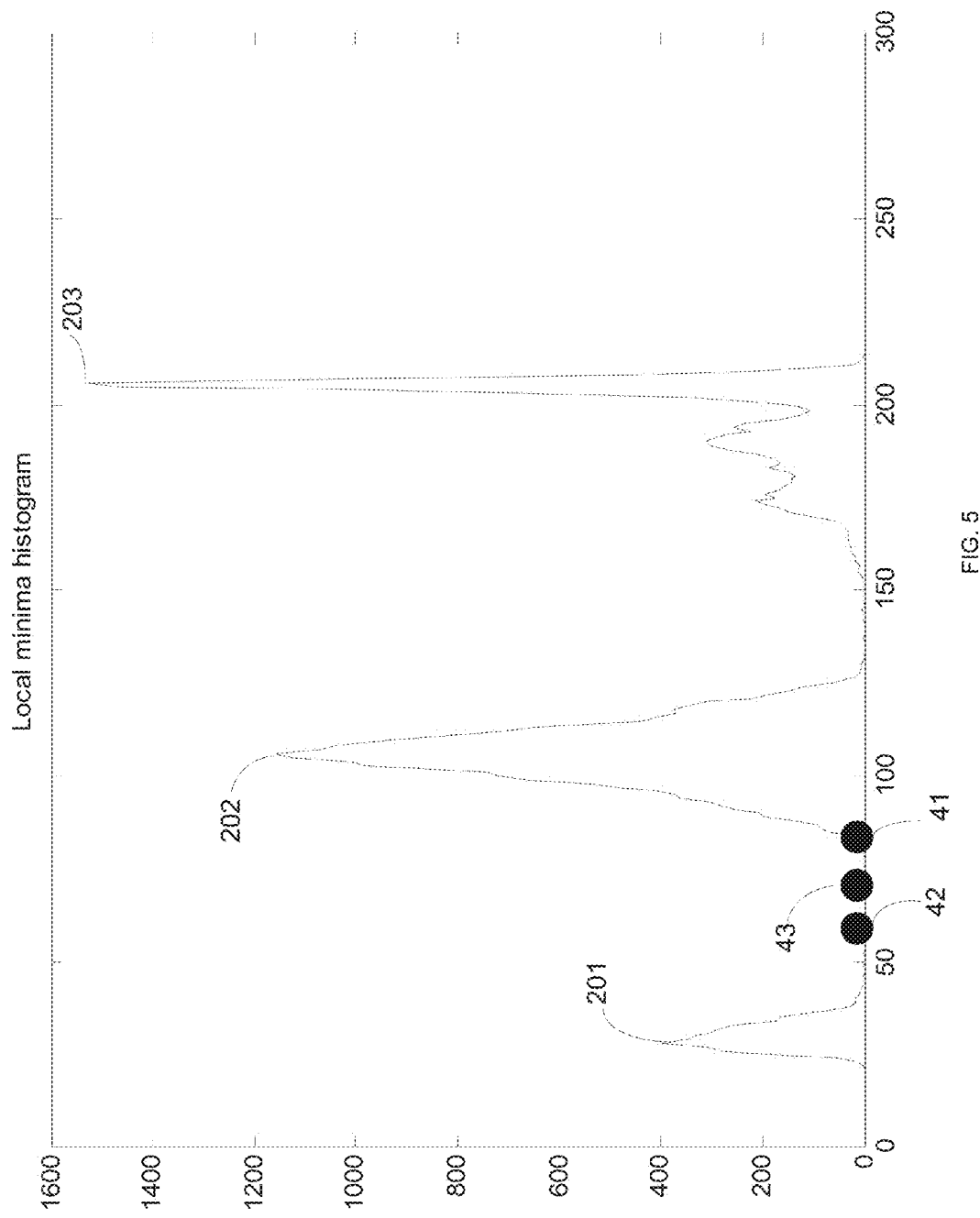
FIG. 5 illustrates a histogram of local minima, an intensity value, a first intensity threshold and a second intensity threshold according to an embodiment of the invention.

FIG. 5 illustrates a histogram of local minima, an intensity value 43, a first intensity threshold 41 and a second intensity threshold 42 according to an embodiment of the invention.

The histogram of local minima provides a mapping between values of local minima (such as local minima 21, 22, 23, 24, 25 and 26 of FIG. 2) and the number of local minima that have the same intensity. The histogram is an example of a distribution of pixels.

The histogram of local minima includes three peaks 201, 202 and 203 that are spaced apart from each other.

The intensity value 43 is received and values of first intensity threshold and the second intensity threshold are calculated during method 300. It may be desired not to include any one of peaks 201, 202 and 203 between the first intensity threshold and the second intensity threshold while maximizing the distance between first intensity threshold and the second intensity threshold—while maintaining the distance below maximal allowable distance.

Step 316 is followed by step 318 of checking whether more values of the first should be evaluated. More values may be evaluated when the number of iterations (of steps 312, 314 and 316) did not reach a predefined number.

If the answer is yes—jumping to step 314 and if the answer is no—jumping to step 320 of selecting the first intensity threshold and the second intensity threshold, out of all first intensity threshold and the second intensity threshold that were examined during steps 314 and 316 in view of the costs. Step 320 may include selecting the first intensity threshold and the second intensity threshold that are associated with the best cost.

Method 300 may be included in method 200.

FIG. 6 illustrates areas 90 and areas 91(1)-91(N) of lithographic mask 9 according to an embodiment of the invention.

Areas 90 are associated with printable features.

Areas 91(1)-91(N) are associated with non-printable features and are positioned at distances D(1)-D(N) 92(1)-92(N) from areas 90.

N is a positive integer that exceeds one.

Distances D(1)-D(N) 92(1)-92(N) differ from each other.

Up till N different lithographic mask inspection process parameters are assigned to areas 91(1)-91(N). The assignment may be responsive to distances D(1)-D(N) 92(1)-92(N).

According to an embodiment of the invention lower sensitivity is associated with areas that are more distant from areas 90.

According to various embodiments of the invention different lithographic mask inspection process parameters may be assigned to different portions of an area that is associated with a printable feature. The different portions may differ from each other by shape, by size, by distance from a center of the area, by distance from a border of the area, and the like.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A system for assigning lithographic mask inspection process parameters, the system comprises a search module, a decision module, and a memory module;
   wherein the memory module is configured to store an expected image that is expected to be formed on a photoresist during a lithographic process that involves illuminating a lithographic mask;
   wherein the search module is configured to search in the expected image for printable features;
   wherein the decision module is configured to assign a first lithographic mask inspection process parameter to lithographic mask areas related to the printable features and assign a second lithographic mask inspection process parameter to at least some lithographic mask areas that are not associated with the printable features; and
   wherein the second lithographic mask inspection process parameter differs from the first lithographic mask inspection process parameter.

2. The system according to claim 1, wherein each printable feature has a local minimum that is below a first intensity threshold and comprises pixels that have intensities that do not exceed a second intensity threshold; and wherein the first intensity threshold is lower than the second intensity threshold.

3. The system according to claim 2, wherein the second intensity threshold is a printability threshold of the lithographic mask.

4. The system according to claim 1, further comprising an inspection module that is configured to inspect the lithographic mask while applying the first lithographic mask inspection process parameter when inspecting lithographic mask areas related to the printable features and to inspect the lithographic mask while applying the second lithographic mask inspection process parameter when inspecting lithographic mask areas that are not associated with the printable features.

5. The system according to claim 1, wherein the first lithographic mask inspection process parameter and the second lithographic mask inspection process parameter define a sensitivity of an inspection process.

6. The system according to claim 1, wherein each printable feature has a local maximum that is above a first intensity threshold and comprises pixels that have intensities that are not lower than a second intensity threshold; and wherein the first intensity threshold is higher than the second intensity threshold.

7. A method for assigning lithographic mask inspection process parameters, the method comprising:
   generating or receiving an expected image that is expected to be formed on a photoresist during a lithographic process that involves illuminating a lithographic mask; searching in the expected image for printable features; and assigning a first lithographic mask inspection process parameter to lithographic mask areas related to the printable features and assigning a second lithographic mask inspection process parameter to at least some lithographic mask areas that are not associated with the printable features, wherein the second lithographic mask inspection process parameter differs from the first lithographic mask inspection process parameter.

8. The method according to claim 7, wherein each printable feature has a local minimum that is below a first intensity threshold and comprises pixels that have intensities that do not exceed a second intensity threshold; and wherein the first intensity threshold is lower than the second intensity threshold.

9. The method according to claim 8, wherein the second intensity threshold is a printability threshold of the lithographic mask.

10. The method according to claim 7, further comprising inspecting the lithographic mask while applying the first lithographic mask inspection process parameter when inspecting lithographic mask areas related to the printable features and inspecting the lithographic mask while applying the second lithographic mask inspection process parameter when inspecting lithographic mask areas that are not associated with the printable features.

11. The method according to claim 7, wherein the first lithographic mask inspection process parameter and the second lithographic mask inspection process parameter define a sensitivity of an inspection process.

12. The method according to claim 7, wherein each printable feature has a local maximum that is above a first intensity threshold and comprises pixels that have intensities that are not lower than a second intensity threshold; and
   wherein the first intensity threshold is higher than the second intensity threshold.

13. A non-transitory computer readable medium that stores instructions that once executed by a computer cause the computer to generate or receive an expected image that is expected to be formed on a photoresist during a lithographic process that involves illuminating a lithographic mask; search in the expected image for printable features; and assign a first lithographic mask inspection process parameter to lithographic mask areas related to the printable features and assign a second lithographic mask inspection process parameter to at least some lithographic mask areas that are not associated with the printable features, wherein the second lithographic mask inspection process parameter differs from the first lithographic mask inspection process parameter.

* * * * *